(12) United States Patent
Zhou et al.

(10) Patent No.: US 11,747,317 B2
(45) Date of Patent: Sep. 5, 2023

(54) UNDERWATER ROBOT WATER QUALITY DATA ACQUISITION DEVICE AND CONTROL METHOD THEREOF

(71) Applicant: ZHEJIANG UNIVERSITY, Hangzhou (CN)

(72) Inventors: Jing Zhou, Hangzhou (CN); Yuchao Che, Hangzhou (CN); Jian Gao, Hangzhou (CN); Liming Zhao, Hangzhou (CN); Haocai Huang, Hangzhou (CN); Ying Chen, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 18/054,918

(22) Filed: Nov. 14, 2022

(65) Prior Publication Data
US 2023/0228727 A1 Jul. 20, 2023

(30) Foreign Application Priority Data

Jan. 17, 2022 (CN) .......................... 202210049740.9

(51) Int. Cl.
| | |
|---|---|
| G01N 33/18 | (2006.01) |
| B63G 8/08 | (2006.01) |
| B63G 8/00 | (2006.01) |
| G16Y 40/10 | (2020.01) |
| G08C 17/02 | (2006.01) |
| B63G 8/04 | (2006.01) |

(52) U.S. Cl.
CPC .......... *G01N 33/1886* (2013.01); *B63G 8/001* (2013.01); *B63G 8/04* (2013.01); *B63G 8/08* (2013.01); *G08C 17/02* (2013.01); *G16Y 40/10* (2020.01); *B63G 2008/002* (2013.01)

(58) Field of Classification Search
CPC .............. G01N 33/1886; G16Y 40/10; B63G 2008/002; G08C 17/02
See application file for complete search history.

(56) References Cited

U.S. PATENT DOCUMENTS

| 4,089,209 A * | 5/1978 | Grana ................ G01N 33/1886 |
| | | 73/61.41 |
| 2002/0054828 A1* | 5/2002 | Keeping .................. G01N 1/14 |
| | | 422/430 |
| 2005/0207939 A1 | 9/2005 | Roussi et al. |

FOREIGN PATENT DOCUMENTS

| CN | 203502404 U | 3/2014 |
| CN | 203502405 U | 3/2014 |

(Continued)

*Primary Examiner* — Stephen P Avila

(57) ABSTRACT

A novel underwater robot water quality data acquisition device includes a casing, a thruster group, an upper cabin, a lower cabin, a buoy cabin, an upper cabin tray, a lower cabin tray, a power supply assembly, a power conditioning module, a data acquisition control module, a water quality sensor assembly, and a wireless Internet of Things (IoT) module. The device can convert the power supply voltage required by each other module through the power management module. The data acquisition control module transmits signals to the water quality sensor assembly in a set timing sequence, performs real-time reading and processing of water quality data fed back from the sensor, and uploads the processed water quality data to the data platform through the wireless IoT module, thereby achieving the display and preservation of water quality data.

9 Claims, 4 Drawing Sheets

(56) References Cited

FOREIGN PATENT DOCUMENTS

| | | |
|---|---|---|
| CN | 108156263 A | 6/2018 |
| CN | 208255062 U | 12/2018 |
| CN | 109506631 A | 3/2019 |
| CN | 109828095 A | 5/2019 |
| CN | 113353216 A | 9/2021 |
| JP | 2009214042 A | 9/2009 |
| WO | 2018198018 A1 | 11/2018 |

* cited by examiner

UNDERWATER ROBOT WATER QUALITY DATA ACQUISITION DEVICE AND CONTROL METHOD THEREOF

CROSS REFERENCE

The present application claims priority of Chinese Patent Application No. 202210049740.9, filed on Jan. 17, 2022, the entire contents of which are hereby incorporated by reference in their entireties.

TECHNICAL FIELD

The present disclosure relates to the field of robots, and in particular to a novel underwater robot water quality data acquisition device and a control method thereof.

BACKGROUND

In recent years, there has been a gradual increase in the invention and application of underwater robots internationally. When underwater, human is limited by physiological factors, resulting in poor flexibility of action, limited diving depth. In addition, the underwater environment in some waters is complex and harsh. In this case, underwater robots can replace human to dive into the water for work, with flexible action and various functions, not limited by various underwater environmental factors. Therefore, this type of robot has broad application prospects in the fields of underwater search and rescue, undersea exploration, military reconnaissance, etc.

Water quality is the most direct characterization data of the water environment within a certain range where the underwater robot works. In ecological protection, the quality of natural water bodies is an important parameter of ecological indicators to reflect the ecological environment in the region, thereby helping pollution prevention and ecological restoration. In fisheries, monitoring water quality parameters in artificial fish farms can help improve management decisions, resulting in improved quality and production.

Combining the above two aspects, small underwater robots equipped with water quality testing function devices have important practical significance. Currently, the main limitations of underwater robots for water quality monitoring are as follows: (1) most research and inventions only achieve water sample collection function and the number of collected samples is small, which makes it impossible to obtain water quality data in real time, with the requirements of repeatedly launching the underwater robots for sampling and supplemented by manual participation in subsequent water quality testing steps; (2) the water quality data cannot be directly processed and stored, and data visualization cannot be achieved, which also increases the number of underwater robot launches and additional data processing and storage steps; (3) unable to obtain dynamic data, i.e., unable to be a one-time access to water quality data of the same sampling point in different time, or unable to obtain data from multiple sampling points in a relatively short period of time.

According to the above-mentioned limitations, a novel underwater robot water quality data acquisition device that both obtains immediate water quality data and uploads data in real time is urgently needed to be designed and applied.

SUMMARY OF THE DISCLOSURE

The purpose of the present disclosure is to propose a new type of underwater robot water quality data acquisition device in order to overcome the insufficiency of the existing underwater robot in the aspect of water quality detection. The water quality data acquisition device has the ability to dive into the waters to be measured with the underwater robot. It is able to detect water quality data such as pH, conductivity, dissolved oxygen, turbidity and chlorophyll in real time at a series of sampling points, process the water quality data and upload it to the Internet of Things (IoT) platform with the help of cellular network, to achieve real-time recording and storage functions, Therefore, it is an efficient, convenient and widely used water quality data collection device.

For achieving the above objectives, the present disclosure proposes the following technical scheme.

A novel water quality data acquisition device of an underwater robot, comprising: a casing, a thruster group, an upper cabin, a lower cabin, a buoy cabin, an upper cabin tray, a lower cabin tray, a power supply assembly, a power conditioning module, a data acquisition control module, a water quality sensor assembly, and a wireless Internet of Things (IoT) module;

Wherein the casing, configured as the outermost layer of the water quality data acquisition device, is not a closed structure, which defines some openings for receiving the thruster group; upper cabin tray and the lower cabin tray are connected to each other to form a mounting bracket, which is disposed inside the casing and is fixedly connected with an inner wall of the casing; the thruster group comprises six thrusters, wherein a propelling direction of four thrusters among the six thrusters is a horizontal direction, and the four thrusters are symmetrically arranged around the mounting bracket, for providing a torque for rotation of the underwater robot around a vertical central axis and a thrust for a horizontal movement of the underwater robot; a propelling direction of remaining two thrusters among the six thrusters is a vertical direction, and the remaining two thrusters are arranged symmetrically on both sides of the mounting bracket, for providing a thrust for a vertical movement of the underwater robot; the upper cabin is fixed at a square slot in the middle of the upper cabin tray, and the lower cabin is fixed at another square slot in the middle of the lower cabin tray; the buoy cabin is configured to float on a sea surface using positive buoyancy; the upper cabin, lower cabin and buoy cabin are each a sealed compartment; the power supply assembly is individually arranged inside the lower cabin; the power conditioning module and the data acquisition control module are integrated on a same circuit board; the wireless IoT module comprises a main circuit and an antenna, the main circuit and the circuit board arranging the power conditioning module and the data acquisition control module are both arranged in the upper cabin, and the antenna is arranged in the buoy cabin; the water quality sensor assembly is arranged on the upper cabin tray;

the data acquisition control module, the water quality sensor assembly, and the wireless IoT module are powered by the power supply assembly; the power conditioning module and the power supply assembly are connected, for adjusting the power supply assembly to output voltage of different levels;

the data acquisition control module and the water quality sensor assembly are connected through a RS485 bus; the data acquisition control module and the main circuit of the wireless IoT module are connected through a serial communication line; the main circuit and the antenna of the wireless IoT module are connected through an ANT interface;

the data acquisition control module is configured to read and process water quality data fed back from a sensor in real time, by transmitting a control signal to the water quality sensor assembly in a set timing sequence; at fixed intervals, the data acquisition control module is configured to upload the processed water quality data to a data platform through the wireless IoT module, to realize real-time displaying and storing of the water quality data.

In some embodiments, the power supply assembly comprises a lithium battery pack and a switch; an output voltage range of the lithium battery pack is 12V; the lithium battery pack is arranged inside the lower cabin; the switch is configured to control an external output of the lithium battery pack, and is arranged on a hatch of the lower cabin.

In some embodiments, the power conditioning module is powered by the power supply assembly, and is configured to realize different voltage levels of direct-current (DC) energy conversion through three circuits: a DC input 12V to DC stable output 12V circuit, a DC input 12V to DC output 5V circuit, and a DC input 5V to DC output 3.3V circuit. The three circuits of the power conditioning module may be cascaded. In some embodiments, the three circuits of the power conditioning module are all wide-range DC input, all allowing DC input of 4.5V to 60V; the three circuits of the power conditioning module is cascaded or separated.

In some embodiments, the data acquisition control module is an embedded system based on an STM32 microcontroller, comprising peripheral circuits comprising an external crystal oscillator circuit, an MAX485 circuit, an LED status indication circuit, an RS485 interface, a filter capacitor circuit, a power interface, a serial communication interface, a voltage regulator circuit, a startup mode circuit, and a reset circuit; the MAX485 circuit is configured to receive, translate and transmit signals between a serial port of the microcontroller and the RS485 bus.

In some embodiments, the water quality sensor assembly comprises water quality sensors: a pH electrode, a conductivity electrode, a dissolved oxygen electrode, a turbidity electrode, and a self-cleaning chlorophyll digital sensor; a power relationship of the water quality sensors is in parallel; signal lines of the water quality sensors are all connected to the RS485 bus.

In some embodiments, the wireless IoT module uses a wireless communication module combined with an IoT application development platform, both of which complete real-time uploading of data through cellular mobile communication.

In some embodiments, a power line between the power supply assembly and the power conditioning module is connected into the lower cabin through a threading bolt; a power line between the power conditioning module and the water quality sensor assembly is connected into the upper cabin through a threading bolt; a power line and a signal line of each water quality sensor in the water quality sensor assembly are each connected into the upper cabin through a threading bolt and connected to the RS485 bus.

The present disclosure further provides a method for controlling a novel water quality data acquisition device, wherein after the switch of the power supply assembly is turned on, the data acquisition control module sends an instruction to start the wireless IoT module, accesses a cellular network, logins to a corresponding account of an IoT platform, sends corresponding parameter reading instructions to the RS485 bus sequentially and cyclically in a certain order and receives instructions returned by corresponding sensors, and check and decode the instructions; at fixed intervals, current water quality data is sent to the IoT platform to update a data model of the IoT platform.

Compared with the prior art, the beneficial effects of the present disclosure are as followed.

(1) The present disclosure's water quality data acquisition device can be carried by an underwater robot to dive into a wide range of waters, and can perform real-time detection on water bodies with a depth of 20 meters. Compared with traditional means of water quality testing, the device can be more convenient for the water quality of larger waters for direct detection, to avoid the inconvenience of sampling; the device carries a variety of water quality sensors, which is fully functional, without the requirements to collect multiple samples, avoiding the impact of changes in water quality on the detection of some parameters after sampling.

(2) The data acquisition control module and the wireless IoT module of the present disclosure can directly process and store water quality data, and can realize the visualization of water quality data in combination with the functions of the IoT platform, avoiding the complicated work of repeatedly launching underwater robots and additional steps of data processing and storage.

(3) The present disclosure can more conveniently acquire the water quality data of the same sampling point at different times in one launch, or simultaneously acquire the data of multiple sampling points in a relatively short period of time, which is more conducive to dynamically monitoring and analyzing small changes in water quality.

Figure 1:
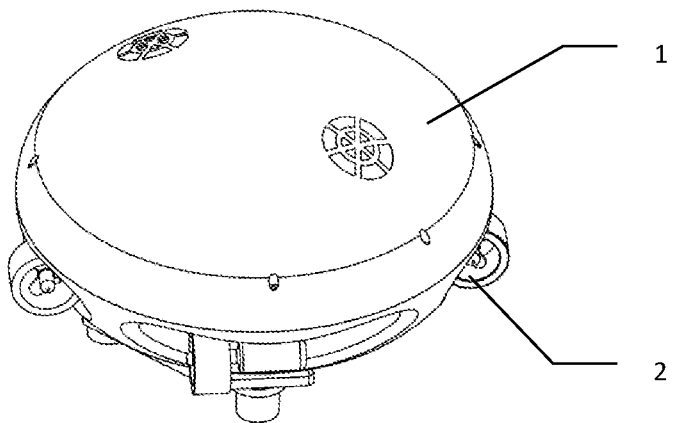
FIG. 1 is an appearance schematic view of a water quality data acquisition device of an underwater robot according to an embodiment of the present disclosure.

Reference numerals: 1 casing, 2 thruster group, 3 upper cabin, 4 lower cabin, 5 upper cabin tray, 6 lower cabin tray, 7-1 intelligent pH electrode, 7-2 intelligent conductivity (EC) electrode, 7-3 smart dissolved oxygen (DO) electrode, 7-4 smart turbidity electrode, 7-5 self-cleaning chlorophyll digital sensor, 8 buoy cabin.

DETAILED DESCRIPTION

The present disclosure will be described in detail below with reference to the accompanying drawings. The technical features of the various embodiments of the present disclosure can be combined correspondingly on the premise that there is no conflict with each other.

As shown in FIGS. 1-3 and 6, in a specific implementation of the present disclosure, a novel water quality data acquisition device of an underwater robot includes a casing 1, a thruster group 2, an upper cabin 3, a lower cabin 4, a buoy cabin 8, an upper cabin tray 5, a lower cabin tray 6, a power supply assembly, a power conditioning module, a data acquisition control module, a water quality sensor assembly, and a wireless Internet of Things (IoT) module.

Figure 2:
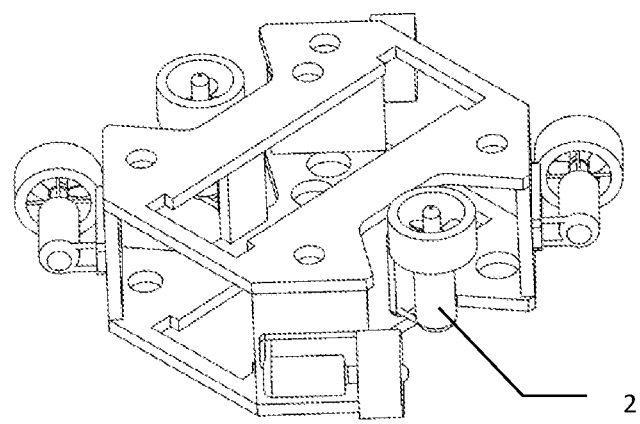
FIG. 2 is a structural schematic view of a mounting bracket and an upper part thereof according to an embodiment of the present disclosure.
Figure 6:
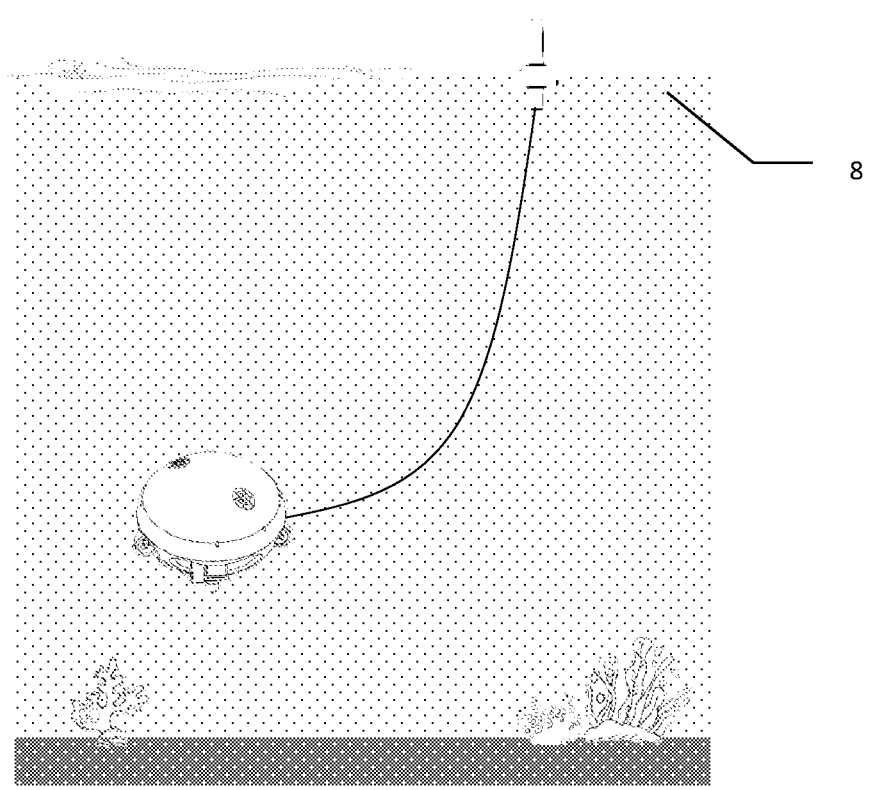
FIG. 6 is a working environment schematic view according to an embodiment of the present disclosure.

In this embodiment, the casing 1 is in the shape of a dish and is arranged on an outermost layer of the water quality data acquisition device. The casing 1 is not a closed structure, and defines an opening for arranging the thruster group 2. Other openings or hollow structures may be defined according to specific needs. The casing 1 is mainly configured to protect an internal structure of the water quality data acquisition device. As shown in FIG. 2, the upper cabin tray 5 and the lower cabin tray 6 are connected to each other to form a mounting bracket, and the mounting bracket is disposed inside the casing 1 and is fixedly connected with an inner wall of the casing 1. The thruster group 2 includes six thrusters in total. A propelling direction of four thrusters among the six thrusters is a horizontal direction, and the four thrusters are symmetrically arranged around the mounting bracket, for providing a torque for rotation of the underwater robot around a vertical central axis and a thrust for horizontal movement of the underwater robot. A propelling direction of the remaining two thrusters among the six thrusters is a vertical direction, and the remaining two thrusters are arranged symmetrically on both sides of the mounting bracket to provide a thrust for vertical movement of the underwater robot. As shown in FIG. 6, the buoy cabin 8 floats on the sea surface using positive buoyancy, and the upper cabin 3, lower cabin 4 and buoy cabin 8 are sealed compartments. The upper cabin 3 is fixed at a square slot in the middle of the upper cabin tray 5, and the lower cabin 4 is fixed at another square slot in the middle of the lower cabin tray 6. The power supply assembly is arranged inside the lower cabin 4. The power conditioning module, the data acquisition control module, and a main circuit of the wireless IoT module are all arranged inside the upper cabin 3. An antenna of the wireless IoT module is arranged in the buoy cabin 8. The water quality sensor assembly is arranged at the upper cabin tray 5. Power lines between the power supply assembly and the power conditioning module are connected through threading bolts on hatches of the upper cabin 3 and the lower cabin 4. A power line between the power conditioning module and the water quality sensor assembly is connected to the upper cabin 3 through the threading bolts. In the water quality sensor assembly, the power line and signal line of each water quality sensor are connected into the sealed compartment through the threading bolts on the hatch of the upper cabin 3.

Figure 5:
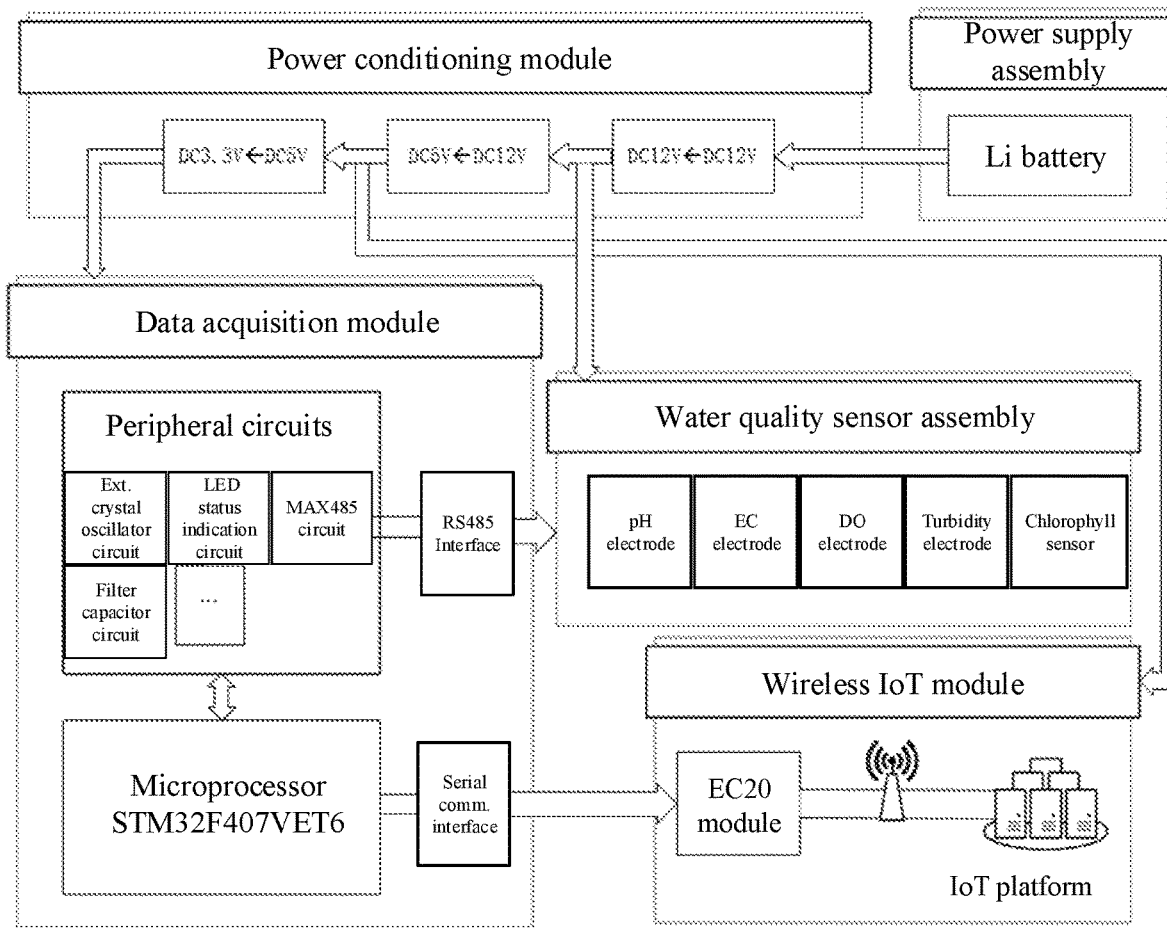
FIG. 5 is a connection view of a power supply assembly, a power conditioning module, a data acquisition control module, a water quality sensor assembly, and a wireless Internet of Things (IoT) module according to an embodiment of the present disclosure.

As shown in FIG. 5, in a specific implementation of the present disclosure, the power supply assembly includes a lithium battery pack and a switch, and an output voltage range of the lithium battery pack is 12V. The lithium battery pack is arranged inside the lower cabin 4. The switch is configured to control an external output of the lithium battery pack, and is arranged on a hatch of the lower cabin 4.

As shown in FIG. 5, the power conditioning module is powered by the power supply assembly, and realizes different voltage levels of DC energy conversion through a DC input 12V to DC stable output 12V circuit, a DC input 12V to DC output 5V circuit, a DC input 5V to DC output 3.3V circuit. The three circuits of the power conditioning module may be cascaded. The three circuits of the power conditioning module are wide-range DC input, all allowing DC input 4.5V to 60V. The three circuits of the power conditioning module may be cascaded or separated.

As shown in FIG. 5, the data acquisition control module is an embedded system based on an STM32 microcontroller, including peripheral circuits such as an external crystal oscillator circuit, an MAX485 circuit, an LED status indication circuit, an RS485 interface, a filter capacitor circuit, a power interface, a serial communication interface, a voltage regulator circuit, a startup mode circuit, a reset circuit, etc. The MAX485 circuit is configured to receive, translate and transmit signals between a serial port of the microcontroller and an RS485 bus.

Figure 3:
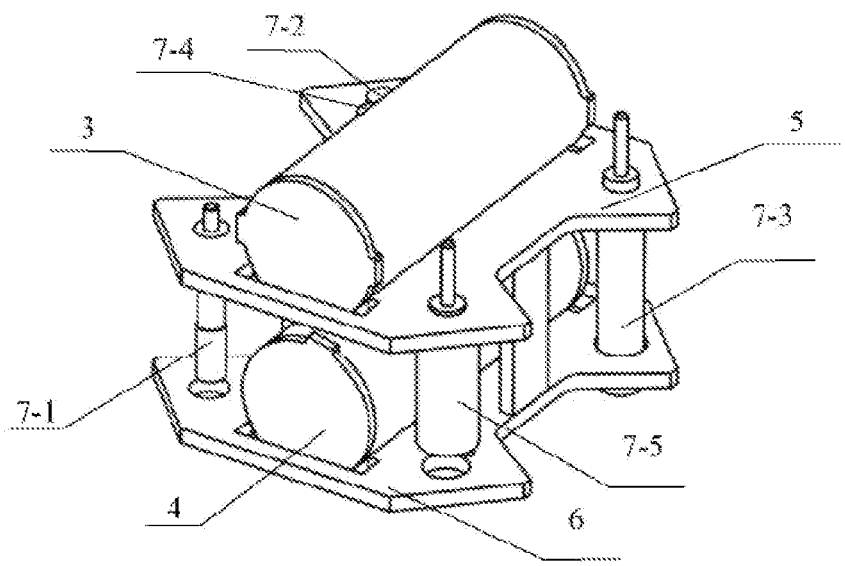
FIG. 3 is another structural schematic view of a mounting bracket and an upper part thereof according to embodiment of the present disclosure.
Figure 4:
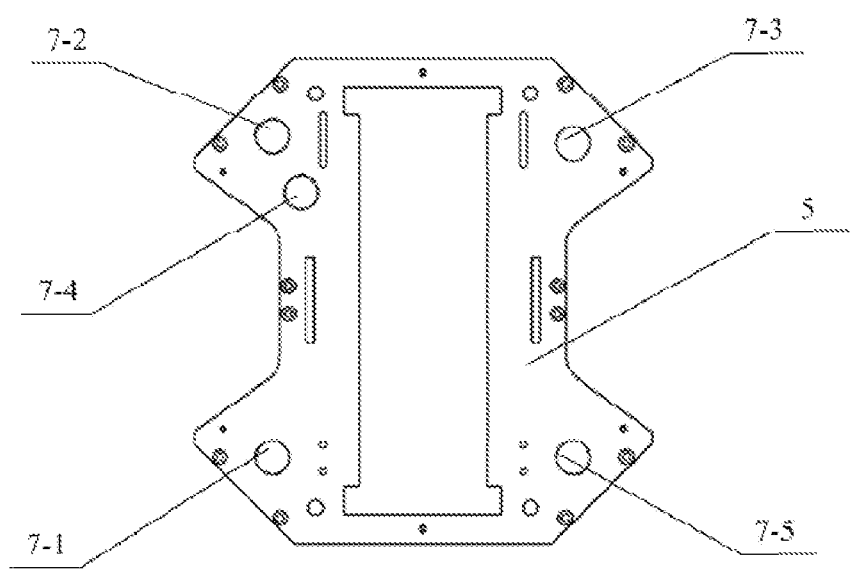
FIG. 4 is a structural schematic view of an upper cabin tray of an underwater robot according to an embodiment of the present disclosure.

As shown in FIGS. 2-4, the water quality sensor assembly includes but is not limited to an intelligent pH electrode 7-1, an intelligent conductivity (EC) electrode 7-2, an intelligent dissolved oxygen (DO) electrode 7-3, an intelligent turbidity electrode 7-4, a self-cleaning chlorophyll digital sensor 7-5, etc., each arranged on the upper cabin tray 5 through a thread on an upper part of the respective sensor. The above sensor electrodes are perpendicular to the cabin tray and surround the upper cabin 3 and the lower cabin 4 at an appropriate distance, as shown in FIGS. 2 and 3. The power relationship of the water quality sensors is in parallel. The signal lines of the water quality sensors are all connected to the RS485 bus.

The working mode of the present disclosure is as follows.

The upper cabin 3 and the lower cabin 4 are respectively fixed in the square slots of the upper cabin tray 5 and the lower cabin tray 6, and both the upper cabin 3 and the lower cabin 4 are sealed compartments.

The switch of the power supply assembly disposed on the hatch of the lower cabin 4 is turned on, and the lithium battery pack supplies power to the entire device circuit. The electrical energy is transmitted to the power conditioning module through the power line, and the input 12V electrical energy is converted, through the DC input 12V to DC stable output 12V circuit, the DC input 12V to DC output 5V circuit, and the DC input 5V to DC output 3.3V circuit, to obtain DC 12V, DC 5V, and DC 3.3V electrical energy, respectively, thereby providing power for the water quality sensor assembly, the wireless IoT module, and the data acquisition control module.

The data acquisition control module is powered on, and the power indicator lights up. The data acquisition control module sends an instruction to start an EC20 module and continuously tries to connect to the cellular network. After connecting and logging into an IoT platform, the program runs normally and the MCU indicator lights up. The data acquisition control module sends corresponding parameter reading instructions to the RS485 bus sequentially and cyclically in a certain order and receives instructions returned by the corresponding sensors. Every time an instruction is sent, the data acquisition control module will wait for the reply instruction from the water quality sensor, and check and decode the instruction, i.e., completing a collection of one item of water quality data. Then the data acquisition control module sends another instruction to collect the next item of water quality data. At fixed intervals, the data acquisition control module sends instructions to the EC20 module, and the EC20 module sends the current water quality data to the IoT platform through the antenna and updates the data model of the IoT platform.

Through real-time data acquisition and wireless IoT technology, the water quality data acquisition device may be equipped on underwater robots to be applied for various types of shallow waters (within 20 m from the sea level). Better than the conventional fixed-point water quality monitoring means, the present disclosure proposes a technical solution which has advantages of easy to operate, diversified data samples, and being able to achieve needs of a real-time and long-term water quality data observation within a larger water area.

The above descriptions are only some embodiments of the present disclosure, and are not intended to limit the scope of the present disclosure. Obviously, those skilled in the art can make various changes and modifications to the present disclosure without departing from the spirit and scope of the present disclosure. In this way, any modification and variation of the present disclosure falling within the scope of the claims and equivalent technologies of the present disclosure should be within the scope of the present disclosure.

What is claimed is:

1. A water quality data acquisition device of an underwater robot, comprising: a casing (1), a thruster group (2), an upper cabin (3), a lower cabin (4), a buoy cabin (8), an upper cabin tray (5), a lower cabin tray (6), a power supply assembly, a power conditioning module, a data acquisition control module, a water quality sensor assembly, and a wireless Internet of Things (IoT) module;

wherein the casing (1), configured as an outermost layer of the water quality data acquisition device, is not a closed structure, which defines some openings for receiving the thruster group (2); the upper cabin tray (5) and the lower cabin tray (6) are connected to each other to form a mounting bracket, which is disposed inside the casing (1) and is fixedly connected with an inner wall of the casing (1); the thruster group (2) comprises six thrusters, wherein a propelling direction of four thrusters among the six thrusters is a horizontal direction, and the four thrusters are symmetrically arranged around the mounting bracket, for providing a torque for rotation of the underwater robot around a vertical central axis and a thrust for a horizontal movement of the underwater robot; a propelling direction of remaining two thrusters among the six thrusters is a vertical direction, and the remaining two thrusters are arranged symmetrically on both sides of the mounting bracket, for providing a thrust for a vertical movement of the underwater robot; the upper cabin (3) is fixed at a square slot in the middle of the upper cabin tray (5), and the lower cabin (4) is fixed at another square slot in the middle of the lower cabin tray (6); the buoy cabin (8) is configured to float on a sea surface using positive buoyancy; the upper cabin (3), lower cabin (4) and buoy cabin (8) are each a sealed compartment; the power supply assembly is individually arranged inside the lower cabin (4); the power conditioning module and the data acquisition control module are integrated on a same circuit board; the wireless IoT module comprises a main circuit and an antenna, the main circuit and the circuit board arranging the power conditioning module and the data acquisition control module are both arranged in the upper cabin (3), and the antenna is arranged in the buoy cabin (8); the water quality sensor assembly is arranged on the upper cabin tray (5);

the data acquisition control module, the water quality sensor assembly, and the wireless IoT module are powered by the power supply assembly; the power conditioning module and the power supply assembly are connected, for adjusting the power supply assembly to output voltage of different levels;

the data acquisition control module and the water quality sensor assembly are connected through an RS485 bus; the data acquisition control module and the main circuit of the wireless IoT module are connected through a serial communication line; the main circuit and the antenna of the wireless IoT module are connected through an ANT interface;

the data acquisition control module is configured to read and process water quality data fed back from a sensor in real time, by transmitting a control signal to the water quality sensor assembly in a set timing sequence; at fixed intervals, the data acquisition control module is configured to upload the processed water quality data to a data platform through the wireless IoT module, to realize real-time displaying and storing of the water quality data.

2. The water quality data acquisition device according to claim 1, wherein the power supply assembly comprises a lithium battery pack and a switch; an output voltage range of the lithium battery pack is 12V; the lithium battery pack is arranged inside the lower cabin (4); the switch is configured to control an external output of the lithium battery pack, and is arranged on a hatch of the lower cabin (4).

3. The water quality data acquisition device according to claim 1, wherein the power conditioning module is powered by the power supply assembly, and is configured to realize different voltage levels of direct-current (DC) energy conversion through three circuits: a DC input 12V to DC stable output 12V circuit, a DC input 12V to DC output 5V circuit, and a DC input 5V to DC output 3.3V circuit.

4. The water quality data acquisition device according to claim 3, wherein the three circuits of the power conditioning module are all wide-range DC input, all allowing DC input of 4.5V to 60V; the three circuits of the power conditioning module are cascaded or separated.

5. The water quality data acquisition device according to claim 1, wherein the data acquisition control module is an embedded system based on an STM32F407VET6 microcontroller, comprising peripheral circuits comprising an external crystal oscillator circuit, an MAX485 circuit, an LED status indication circuit, an RS485 interface, a filter capacitor circuit, a power interface, a serial communication interface, a voltage regulator circuit, a startup mode circuit, and a reset circuit; the external crystal circuit is connected to pins 12 and 13 of the microcontroller; the MAX485 circuit is connected to pins 47 and 48 of the microcontroller in the form of a serial port and to the RS485 interface in the form of a bus for receiving, translating and sending signals between a serial port of the microcontroller and the RS485 bus; the LED status indication circuit is connected to a power supply line, ground, and pin 23 of the microcontroller; the filter capacitor circuit is connected to a high level and the ground of the power supply line of the microcontroller; the power interface is connected to the high level and the ground of the power supply line of the microcontroller; the serial communication interface is connected to pins 25 and 26 of the microcontroller; in the peripheral circuits, the voltage regulator circuit is connected to pins 47 and 79 of the microcontroller, the startup mode circuit is connected to pin 94 of the microcontroller, and the reset circuit is connected to pin 14 of the microcontroller.

6. The water quality data acquisition device according to claim 1, wherein the water quality sensor assembly comprises water quality sensors: a pH electrode (7-1), a conductivity electrode (7-2), a dissolved oxygen electrode (7-3), a turbidity electrode (7-4), and a self-cleaning chlorophyll digital sensor (7-5); a power relationship of the water quality sensors is in parallel; signal lines of the water quality sensors are all connected to the RS485 bus.

7. The water quality data acquisition device according to claim 1, wherein the wireless IoT module is configured to achieve a real-time upload of data via cellular mobile communication.

8. The water quality data acquisition device according to claim 1, wherein a power line between the power supply assembly and the power conditioning module is connected into the lower cabin (4) through a threading bolt; a power line between the power conditioning module and the water quality sensor assembly is connected into the upper cabin (3) through a threading bolt; a power line and a signal line of each water quality sensor in the water quality sensor assembly are each connected into the upper cabin (3) through a threading bolt.

9. A method for controlling a water quality data acquisition device according to claim 1, wherein after the switch of the power supply assembly is turned on, the data acquisition control module sends an instruction to start the wireless IoT module, accesses a cellular network, logins to a corresponding account of an IoT platform, sends corresponding parameter reading instructions to the RS485 bus sequentially and cyclically in a certain order and receives instructions returned by corresponding sensors, and check and decode the instructions; at fixed intervals, current water quality data is sent to the IoT platform to update a data model of the IoT platform.

\* \* \* \* \*